(12) United States Patent
Langer et al.

(10) Patent No.: US 9,173,732 B2
(45) Date of Patent: *Nov. 3, 2015

(54) MEDICAL DEVICES FOR USE IN THE SURGICAL TREATMENT OF HYPERPROLIFERATIVE DISEASES AFFECTING THE SPINAL CORD

(75) Inventors: Robert S. Langer, Newton, MA (US); Rajiv Saigal, Philadelphia, PA (US); Yang Teng, Wellesley, MA (US); Eric Woodard, Jamaica Plain, MA (US)

(73) Assignees: The Children's Medical Center Corporation, Boston, MA (US); Massachusetts Institute of Technology, Cambridge, MA (US)

(*) Notice: Subject to any disclaimer, the term of this patent is extended or adjusted under 35 U.S.C. 154(b) by 872 days.

This patent is subject to a terminal disclaimer.

(21) Appl. No.: 12/186,346

(22) Filed: Aug. 5, 2008

(65) Prior Publication Data
US 2009/0053284 A1 Feb. 26, 2009

Related U.S. Application Data

(63) Continuation-in-part of application No. 11/789,538, filed on Apr. 25, 2007.

(60) Provisional application No. 60/794,986, filed on Apr. 25, 2006.

(51) Int. Cl.
*A61F 2/02* (2006.01)
*A61L 27/50* (2006.01)
(Continued)

(52) U.S. Cl.
CPC . *A61F 2/02* (2013.01); *A61L 27/18* (2013.01); *A61L 27/50* (2013.01); *A61L 27/58* (2013.01); *A61F 2210/0004* (2013.01); *A61L 2430/38* (2013.01)

(58) Field of Classification Search
USPC .......................................... 604/500
See application file for complete search history.

(56) References Cited

U.S. PATENT DOCUMENTS 4,950,258 A 8/1990 Kawai et al.
4,955,893 A 9/1990 Yannas et al.
(Continued)

FOREIGN PATENT DOCUMENTS

EP 1084720 A1 3/2001
WO 99/18892 4/1999 ................ A61F 2/28
(Continued)

OTHER PUBLICATIONS

Teng et al., "Functional recovery following traumatic spinal cord injury mediated by a unique polymer scaffold seeded with neural stem cells", Mar. 5, 2002, Proceedings of the National Academy of Sciences, vol. 99, No. 5, pp. 3024-3029.*

(Continued)

*Primary Examiner* — Michael B Pallay
(74) *Attorney, Agent, or Firm* — Fish & Richardson P.C.

(57) ABSTRACT

Provided herein are new methods for the treatment of hyperproliferative diseases affecting the spinal cord, including the use of biodegradable polymers to treat spinal cord tumor recessing, i.e., to patch open zones left by spinal tumor removal. Biocompatible polymeric materials are tailored to fill areas previously occupied by tumors, e.g., materials in the form of tubular articles configured for insertion into the spinal column after surgical removal of a tumor. These protective articles may also include medicinal agents that stimulate spinal column neural regeneration, such as medicines or donor neuronal cells such as human neural stem cells, thus assisting patients to recover motorsensory function after spinal tumor surgery.

23 Claims, 2 Drawing Sheets

(51) Int. Cl.
A61L 27/58 (2006.01)
A61L 27/18 (2006.01)

(56) References Cited

U.S. PATENT DOCUMENTS

| | | | |
|---|---|---|---|
| 5,226,914 A | | 7/1993 | Caplan et al. |
| 5,670,151 A | * | 9/1997 | Larrick et al. ............. 424/183.1 |
| 6,095,148 A | | 8/2000 | Shastri et al. |
| 6,613,089 B1 | | 9/2003 | Estes et al. |
| 6,696,575 B2 | | 2/2004 | Schmidt et al. |
| 8,858,966 B2 | * | 10/2014 | Langer et al. ................. 424/400 |
| 2002/0137706 A1 | | 9/2002 | Evans et al. |
| 2003/0066987 A1 | | 4/2003 | Schmidt et al. |
| 2003/0204197 A1 | | 10/2003 | Onyekaba et al. |
| 2005/0085790 A1 | | 4/2005 | Guest et al. |
| 2005/0251267 A1 | | 11/2005 | Winterbottom et al. |
| 2006/0002978 A1 | | 1/2006 | Shea et al. |
| 2006/0036253 A1 | | 2/2006 | Leroux et al. |
| 2006/0100647 A1 | | 5/2006 | Doi et al. |
| 2007/0213701 A1 | | 9/2007 | Kraft |
| 2007/0243228 A1 | | 10/2007 | McKay |
| 2007/0259020 A1 | | 11/2007 | Langer et al. |
| 2008/0183292 A1 | | 7/2008 | Trieu |

FOREIGN PATENT DOCUMENTS

| | | | |
|---|---|---|---|
| WO | 02/076288 | 10/2002 | |
| WO | 2007/084609 | 7/2007 | ................ A61F 2/28 |
| WO | 2007/127790 A2 | 11/2007 | |

OTHER PUBLICATIONS

Woerly et al., "Spinal cord repair with PHPMA hydrogel containing RGD peptides (NeuroGelTM)", May 2001, Biomaterials, vol. 22, issue 10, pp. 1095-1111.*

Oudega et al., "Axonal regeneration into Schwann cell gra within resorbable poly(alpha-hydroxyacid) guidance channels in the adult rat spinal cord", May 2001, Biomaterials, vol. 22, issue 10, pp. 1125-1136.*

Tsai et al., "Synthetic Hydrogel Guidance Channels Facilitate Regeneration of Adult Rat Brainstem Motor Axons after Complete Spinal Cord Transection", 2004, Journal of Neurotrauma, vol. 21, No. 6, pp. 789-804.*

Harris et al., Spinal Deformity after Spinal Cord Surgery, Paraplegia, 6(4), 232-38 (1969).

International Search Report from PCT/US2008/07226 by Langer et al. (Apr. 21, 2009).

Written Opinion from PCT/US2008/072226 by Langer et al. (Apr. 21, 2009).

Maquet et al. (Poly(D,L-lactide) forms modified by poly(ethylene oxide)-block-poly(D, L-lactide) copolymers and a-FGF: in vitro and in vivo evaluation for spinal cord regeneratin, Biomaterials, 2001, 1137-1146.

Moore et al., "Multiple-channel scaffolds to promote spinal cord axon regeneration," Biomaterials 27, 419-29 (2006).

Yang et al., "Neurotrophin releasing single and multiple lumen nerve conduits," Journal of Controlled Release 104, 433-46 (2005).

Redmond et al., Proceedings of the National Academy of Science, vol. 104, No. 29, 12175-80 (Jul. 17, 2007).

Teng et al., Proceedings of The National Academy of Sciences, vol. 99, 3024-29 (Mar. 2002).

Oudega et al., Biomaterials, vol. 10, 1125-36 (May 2001).

Borgens et al., J. Neurosci. Res., vol. 76, 141-54 (2004).

Luo et al., Neurosci. Lett., vol. 359, 167-70 (2004).

Gautier et al., J. Biomed. Mater. Res., vol. 4, 642-54 (Dec. 1998).

Hiraizumi et al., SPINE, vol. 21, 2272-77 (1995).

Tsai et al., Biomaterials, vol. 27, 519-33 (2006).

Kotwal et al., "Electrical Stimulation Alters Protein Adsorption and Nerve Cell Interactions with Electrically Conducting Biomaterials", Biomaterials, vol. 22, No. 10, pp. 1055-1064, 2001.

Novikova et al., "Biopolymers and Biodegradable Smart Implants for Tissue Regeneration After Spinal Cord Injury", Current Opinion in Neurology, vol. 16, No. 6, pp. 711-715, 2003.

Schmidt et al., "Stimulation of Neurite Outgrowth Using an Electrically Conducting Polymer", Proc. Natl. Acad. Sci. USA, vol. 94, No. 17, pp. 8948-8953, 1997.

Wang et al., Evaluation of Biocompatibility of Polypyrrole In Vitro and In Vivo, J. Biomed Mater Res. A, vol. 68, No. 3, pp. 411-422, 2004.

Supplementary European Search Report; Messemanne, Jasmine; European Patent Office (EP0); Examiner, Publication issued; Jun. 6, 2012; EP07761270; 7 pages.

Office Action, Chinese Patent Application 200780022752.6, Mar. 15, 2013 (translation).

Igaku-Shoin, "Igaku Daijiten," 2003, p. 1386 (notes: Japanese medical dictionary—translation).

Japanese Office Action for JP Application No. 2011-522037 dated Jan. 18, 2013.

Office Action, Japanese Patent Application No. 2009-507940, Jul. 27, 2012.

Search Report and Written Opinion, Singapore Patent Application No. 201100824-0, 18 pages, Aug. 21, 2012.

English Translation: Igaku-Shoin, "Igaku Daijiten," 2003, p. 1386 (notes: Japanese medical dictionary).

Office action issued in Canadian Patent Application No. 2,650,804 on Aug. 12, 2013 (3 pages).

Wang et al., "In vivo evaluation of a novel electrically conductive polypyrrole/poly(D,L-lactide) composite and polypyrrole-coated poly(D,L-lactide-co-glycolide) membranes," Journal of Biomedical Research Part A, 70 A(1): 28-38 (2004).

Search Report and Written Opinion issued in Singapore Patent Application No. 201105406-1 on Jul. 19, 2013 (15 pages).

Office Action issued in Chinese Patent Application No. 200880131305.9 on Mar. 5, 2013 (translation) (9 pages).

English translation of Office Action issued in Korean application No. 10-2008-7028672 issued on Jul. 10, 2013 (11 pages).

George et al., "Fabrication and biocompatibility of polypyrrole implants suitable for neural prosthetics," Biomaterials, 26:3511-3519 (2005).

Office Action issued in CN 200780022752.6 on Aug. 14, 2013 (6 pages) (with translation).

Office Action issued in Korean Patent Application No. 10-2008-7028672 on Sep. 3, 2014 with translation (6 pages).

Office Action issued in JP2011-522037 on Oct. 25, 2013 (translation) (3 pages).

Office Action issued in SG201100824-0 on Dec. 26, 2013 (10 pages).

Office Action issued in EP 07761270.3 on Jan. 20, 2014.

Examination Report issued in SG2011054061 on Apr. 28, 2014 (6 pages).

Huang and Huang, "Biomaterials and Strategies for Nerve Regeneration," Artificial Organs, 30(7):514-522 (2006).

Lavik, Erin Baker, "Functional Recovery Following Traumatic Spinal Cord Injury Mediated by a Novel Polymer Scaffold Seeded with Neural Stem Cells," Submitted to the Department of Materials Science and Engineering in partial fulfillment of the requirements for the Degree of Doctor of Science in Materials Science and Engineering, Massachusetts Institute of Technology (Jun. 2001).

Lee et al., "Three-Dimensional Cell Culture Matrices: State of the Art," Tissue Engineering: Part B, 14(1):61-86 (2008).

Liu et al., "A self-assembling peptide reduces glial scarring, attenuates post-traumatic inflammation and promotes neurological recovery following spinal cord injury," Acta Biomaterialia, 9:8075-8088 (2013).

Madigan et al., "Current tissue engineering and novel therapeutic approaches to axonal regeneration following spinal cord injury using polymer scaffolds," Respiratory Physiology & Neurobiology, 169:183-199 (2009).

Office Action issued in AU2008360388 on Apr. 14, 2014 (3 pages).

Office Action issued in AU2012227370 on Jan. 10, 2014 (3 pages).

Office Action issued in CA2,650,804 on Jul. 7, 2014 (2 pages).

(56) References Cited

OTHER PUBLICATIONS

Schmidt and Leach, "Neural Tissue Engineering: Strategies for Repair and Regeneration," Annu. Rev. Biomed. Eng., 5:293-347 (2003).
Translation of Office Action issued in KR10-2008-7028672 on May 1, 2014 (2 pages).
Zhong and Bellamkonda, "Biomaterials for the central nervous system," J. R. Soc. Interface, 5:957-975 (2008).
Office Action issued in Indian Patent Application No. 5785/CHENP/2008 on Jan. 22, 2015 (2 pages).
Office Action issued in Korean Patent Application No. 10-2011-7005148 on Nov. 25, 2014 with translation (10 pages).
Office Action issued in CA2,650,804 on Apr. 13, 2015 (3 pages).
Office Action issued in KR10-2014-7024979 on Apr. 17, 2015 with English Translation (4 pages).
Reynolds, Francis M., "InVivo Therapeutics Corporation", Submitted to the Sloan School of Management in Partial Fulfillment of the Requirements for the Degree of Master in Business Administration in Conjunction with the Sloan Fellows Program in Innovation and Global Leadership, 2006 (100 pages).

* cited by examiner

Surgical introduction of
the mini-tube

Fig. 2

MEDICAL DEVICES FOR USE IN THE SURGICAL TREATMENT OF HYPERPROLIFERATIVE DISEASES AFFECTING THE SPINAL CORD

CROSS REFERENCE TO RELATED APPLICATIONS

This application is a continuation-in-part of copending U.S. patent application Ser. No. 11/789,538, filed on Apr. 25, 2007, which claims the priority of U.S. Patent Application No. 60/794,986, filed on Apr. 25, 2006, the contents of which are incorporated herein by reference in their entirety.

FIELD

This application generally relates to medical devices and more specifically relates to medical devices for use in the surgical treatment of hyperproliferative diseases affecting the spinal cord.

BACKGROUND

Hyperproliferative diseases of the spinal cord including spine and spinal cord tumors encompass a diverse group of pathologic diagnoses that differ markedly based on the location and age of the patients. Spine and spinal cord can be affected by primary and metastatic tumors, making the differential diagnosis and treatment options extensive. Spinal tumors are often characterized based on their primary location: extradural, intradural-extramedullary, and intramedullary tumors. For instance, spinal cord epidural metastasis ("SEM") is a common complication of systemic cancer with an increasing incidence. Prostate, breast, and lung cancer are the most common offenders.

Metastases usually arise in the posterior aspect of vertebral body with later invasion of epidural space. Metastatic epidural spinal cord compression ("MESCC") and the incidence of spinal metastases are becoming a more common clinically encountered entity as advancing systemic antineoplastic treatment modalities improve survival in cancer patients.

Historically, surgery for spinal metastases has included simple decompressive laminectomy with concomitant spinal stabilization. Results obtained in retrospective case series, however, have shown that this treatment provides little benefit to the patient. With the advent of better patient-related selection practices, in conjunction with new surgical techniques and improved postoperative care, the ability of surgical therapy to play an important and beneficial role in the multidisciplinary care of cancer patients with spinal disease has improved significantly. A continuing and unmet need exists for suitable medical devices that may be used to patch opened spinal cord parenchyma left behind after tumor removal, and more generally, for medical devices useful in the surgical treatment of hyperproliferative diseases affecting the spinal cord.

SUMMARY

Provided herein are new methods for the treatment of hyperproliferative diseases affecting the spinal cord, including the use of biodegradable polymers to treat spinal cord tumor recessing, i.e., to patch open zones left by spinal tumor removal. Biocompatible polymeric materials are tailored to fill areas previously occupied by tumors, e.g., materials in the form of tubular articles configured for insertion into the spinal column after surgical removal of a tumor. These protective articles may also include medicinal agents that stimulate spinal column neural regeneration, such as medicines or donor neuronal cells such as human neural stem cells, thus assisting patients to recover motorsensory function after spinal tumor surgery.

Accordingly, in an embodiment, a method for the treatment of hyperproliferative diseases affecting the spinal cord includes medical treatment of an animal or human subject in need thereof, including steps of removing at least a portion of a tumor from a locus of an animal or human spinal column, and thereafter implanting a polymeric biocompatible article into the spinal column of the animal or human, wherein the polymeric biocompatible article is biodegradable or bioabsorbable in vivo.

In another embodiment, a method of medical treatment of an animal or human subject in need thereof includes steps of removing at least a portion of a tumor from a locus within an animal or human spinal column, molding a polymeric biocompatible material consisting essentially of a single scaffold article comprising poly(lactic-co-glycolic acid), and thereafter implanting the polymeric biocompatible material into the spinal column of the animal or human proximate to (e.g., at least partially surrounding) the locus such that the polymeric biocompatible material at least partially surrounds the locus of the tumor after surgical recessing thereof.

In yet another embodiment, a method of medical treatment of an animal or human subject in need thereof includes steps of surgically exposing a surgical site to provide surgical access to a spinal column containing a tumor, resecting (e.g., excising) at least a portion of the tumor thereby providing an implantation site for a polymeric biocompatible article, implanting the polymeric biocompatible article into the implantation site, and thereafter surgically closing the surgical site.

In a still further embodiment, a method of medical treatment of an animal or human subject in need thereof includes a step of instructing a medical caregiver to implant a polymeric biocompatible article into a spinal column of an animal or human subject after surgical recessing of at least a portion of a tumor from the spinal column (e.g., excising at least a portion of a tumor or surrounding tissue).

Additional features may be understood by referring to the accompanying drawings, which should be read in conjunction with the following detailed description and examples.

DETAILED DESCRIPTION

Described herein are medical devices and methods for mitigating secondary injury to, and promoting recovery of, spinal cord injuries such as those incident to surgery to remove a spinal tumor. More particularly, certain embodiments hereof are directed to polymeric mini-tubes and other articles that may be used in spinal cord tumor resection surgery. In addition, other embodiments are directed to polymeric "fill-in" bandages that may be used for the treatment of spinal cord surgeries. For example, an erodible, or biodegradable, form of biocompatible polymer is fabricated for surgical implantation into the spinal cord following surgical removal of a spinal tumor.

Spinal Cord Tumors

Hyperproliferative diseases affecting the spinal cord include spinal tumors, i.e., growths of cells (neoplasms or masses, whether benign or malignant) within or surrounding the spinal cord. They occur inside the cord (intramedullary), within the meninges (membranes) covering the spinal cord (extramedullary-intradural), between the meninges and the bones of the spine (extradural), or they may extend from other locations, although most spinal tumors are extradural. Metastatic tumors often progress quickly, while primary extramedullary tumors may progress slowly over weeks to years before causing clinically significant nerve damage.

Primary tumors originate in the spine, and secondary tumors result from metastasis from other locations, e.g., the lung, breast, prostate, kidney, or thyroid, although their exact etiology is typically unknown. Any type of tumor may occur in the spine, including lymphoma, leukemic tumors, myeloma, and others. Some spinal tumors occur within the nerves of the spinal cord itself, most often ependymomas and other gliomas. Of the intradural type, many are outside the spinal cord (extramedullary). Intradural tumors are almost always primary CNS tumors, whereas most extradural tumors are either metastatic or primary bone tumors of the spine. The majority of neoplastic conditions that affect the spine are extradural metastases, while most primary spinal axis tumors are intradural. Of these, the intradural extramedullary schwannomas and meningiomas are the most common. Schwannomas and meningiomas are normally intradural, but occasionally they may occur as extradural tumors. Other intradural extramedullary tumors include vascular tumors, chordomas, and epidermoids. Intramedullary tumors often have the same cellular origins as brain tumors. Ependymomas commonly occur as intramedullary tumors, as well as astrocytomas, oligodendrogliomas, gangliogliomas, medulloblastomas, and hemangioblastomas.

The onset of symptoms is gradual, and initial clinical presentation is often asymmetric with non-specific motor weakness predominating. Indeed, manifest pain is frequently difficult to clinically differentiate from commonplace, ordinary musculoskeletal symptoms, which causes diagnostic delay. The level of impairment is determined by the muscle groups involved. Growing tumors affect spinal cord cells, nerve roots, meninges, blood vessels, and bones of the spine (vertebrae), resulting in symptoms associated with compression of the spinal cord or nerve roots, invasion of normal cells by the tumor, or ischemia resulting from blockage of blood vessels. Most primary spinal axis tumors produce symptoms and signs as a result of spinal cord and nerve root compression rather than because of parenchymal invasion.

Symptoms vary depending on the location, type of the tumor, and the general health of the affected animal or human patient. Intramedullary tumors are usually associated with more pronounced symptoms, sometimes over large portions of the body. Spastic weakness may be present with increased muscle tone and abnormal reflexes. Pain sensation in particular dermatomes may be lost simultaneously with, or independently of, other motorsensory losses. Typical symptoms include back pain especially in the middle or lower back, abnormal sensations (paresthesia), muscle weakness, contractions or spasms (fasciculations), cold sensation of the legs, cool fingers or hands, or coolness of other areas. Tumors occurring within the cord (intradural-intramedullary) tend to produce weakness, increased tone usually in the form of spasticity, and sensory loss. Extramedullary lesions often cause radicular pain from nerve root (lower motor neuron) compression, as well as long tract (upper motor neuron) signs from cord compression.

Although each tumor type exhibits a predilection for certain spinal regions (cervical, thoracic, and lumbosacral spine), as a group spinal tumors are distributed almost evenly along the spinal axis. A neurologic examination may indicate the location of the tumor. Radiologic examination (X-ray, CT, MRI) may confirm spinal tumor, although a myelogram (an X-ray or CT scan after dye has been inserted into the spinal fluid) may be needed to isolate the location of the spinal tumor. Likewise, cerebrospinal fluid ("CSF") examination may reveal tumor cells. In particular, MRI is invaluable for the diagnosis, localization, and characterization of spinal tumors. For vascular tumors (e.g., hemangioblastomas) angiography may provide preoperative information about delineation of the tumor blood supply. Whichever diagnostic medical imaging techniques are used, determination of the location of the tumor and its exact relation to the spinal cord is important in surgical planning.

Surgery of Spinal Cord Tumors

At present, radiation therapy and surgical recessing are the only available medical interventions available for spinal cord tumors. Radiation therapy may be used as adjunct therapy for unresectable and incompletely resected neoplasms of the spinal column. Unfortunately, there have been essentially no controlled clinical trials of chemotherapy for primary spinal axis tumors. Theoretically, chemotherapy regimens effective against brain tumors may be assumed to be equally efficacious against histologically identical tumors in the spinal cord. Current clinical experience, however, has been disappointing because primary spinal cord tumors do not respond to chemotherapy as well as their intracranial counterparts. Because of the lack of effective chemotherapies, in most cases surgery is necessary, especially to relieve compression on the spinal cord.

Corticosteroids, such as dexamethasone, reduce inflammation and swelling and may temporarily reduce symptoms. Corticosteroids may be given before, during, and after spinal cord tumor surgery to help control spinal cord edema. Likewise, physical therapy and other interventions may be needed to improve muscle strength and to improve the ability to function independently when permanent neurologic losses occur. Accordingly, surgical treatment seeks to reduce or prevent nerve damage from compression of the spinal cord.

Some tumors can be completely removed by surgery, but in other cases it may be medically acceptable to remove only a portion of the tumor. Some spinal axis tumors, such as most benign intradural spinal neoplasms, and can often be totally excised surgically. Of course, surgical tumor recessing is more effective with early diagnosis and treatment, although nerve damage may persist even after surgery. In order to mitigate against the likelihood of permanent disability, the new surgical treatment methods and materials described herein limit permanent damage to nerves, reduce disability from nerve damage, and promote healing after spinal tumor surgery.

A variety of surgical techniques for spinal tumor recessing are known. An operating microscope is essential for spinal cord tumor surgery, and intraoperative ultrasonography, carbon dioxide lasers, and ultrasonic aspirators are valuable during recessing of spinal cord tumors. During surgery, the spinal cord is examined through either intact or open dura to find the level of maximum tumor involvement and to differentiate tumor cysts from solid tumor masses. In some cases, if a tumor is discovered to be malignant or inoperable, surgery may be aborted.

Tumors that occur in the intradural extramedullary spinal compartment can be completely resected (e.g., surgically removed) through a laminectomy. In many cases, they readily separate away from the spinal cord, which is displaced but not invaded by the tumor. Extraspinal tumor extensions can be removed by broadening the initial laminectomy exposure laterally, whereas others require a separate operation (thoracotomy, costotransversectomy, or a retroperitoneal approach). Anterior cervical tumors can be removed via an anterior approach using corpectomy of the appropriate vertebral levels, followed by strut grafting after the tumor recessing.

Intramedullary tumors are usually also approached through a laminectomy. After dural opening, a longitudinal myelotomy is made, usually in the midline or dorsal root entry zone. The incision is deepened several millimeters to the tumor surface. Dissection planes around the tumor are sought microsurgically and extended gradually around the tumor's surface, followed by removal of the central tumor bulk. Tumors without clear dissection planes often cannot be removed completely, but bulk reduction may provide long-term palliation and nevertheless be medically sufficient.

Spinal Cord Trauma Resulting from Surgery Thereof

Despite the expertise and skill of the surgeon, insult to the spinal cord invariably results from spinal tumor surgery. For example, post-operative bleeding, fluid accumulation, and swelling may occur inside the spinal cord or outside the spinal cord but within the vertebral canal. Pressure from the surrounding bone and meninges can further damage the spinal cord. Moreover, edema of the cord itself can additionally accelerate secondary tissue loss. The primary mechanical injury associated with spinal surgery initiates a cascade of secondary injury mechanisms, including excessive excitatory neurotransmitter accumulation; edema; electrolyte shifts, including increased intracellular calcium; free radical production, especially oxidant-free radicals; and eicosanoid production. In a two-step process, a primary mechanical spinal cord injury results from tumor recessing, resulting from inadvertent and unavoidable trauma to the spinal column, compression, insult, or injury. A secondary injury is cellular and biochemical, in which cellular and molecular processes cause tissue destruction. By interrupting these second processes and diffusing compression resulting from the primary mechanical lesion, as well as any cord edema, healing is promoted.

Secondary pathological events caused by excitotoxicity, free-radical formation, and lack of neurotrophic support include glial scarring, myelin-related axonal growth inhibition, demyelination, and secondary cell death (e.g., apoptosis). For example, oligodendrocyte death may continue after spinal tumor recessing. An environment antagonistic to axonal regeneration is subsequently formed. In addition to damaged regeneration pathways, reflexia hyperexcitability, and muscle spasticity, there are further complications of respiratory and bladder dysfunction, among others. Over time, muscle mass may be lost as a result of loss of innervations and non-use. The end result of these spinal cord insults is lost function, the extent of which is determined by the severity of the spinal cord surgical trauma, as well as by incidental secondary injuries. Even in the case of incomplete motor function loss, common problems include poor posture, reduced walking speed, abnormal balance and gait, and lack of sufficient weight-bearing.

There exists a need to provide improved devices and methods to impede the processes that drive secondary injury at the primary spinal tumor recessing site and otherwise promote post-operative healing. Furthermore, there exists a need for devices and methods that alleviate or mitigate the injurious consequences of spinal tumor recessing, including secondary tissue destruction, edema formation, and influx of inflammatory factors, among others. In addition, a need exists for new technologies that protect spared tissue and promote endogenous healing and repair in order to mitigate functional deficits resulting from removal of spinal cord tumors.

Biocompatible Polymeric Articles for Use in Spinal Cord Tumor Surgery

Described herein are new methods for the treatment of hyperproliferative diseases affecting the spinal cord, including the use of biodegradable polymers to treat spinal cord tumor recessing, i.e., to patch open zones left after spinal tumor removal. Polymeric biocompatible materials and articles are tailored to fill areas previously occupied by tumors, e.g., materials in the form of tubular articles configured for insertion into the spinal column after surgical removal of a tumor therefrom.

For example, an erodible or biodegradable or bioabsorbable form of a biocompatible polymer may be fabricated into a mini-tube for surgical implantation into the site of a spinal cord tumor. Surgical implantation results in a target area that is encapsulated by the polymer, resulting in complete encapsulation of the locus from which the spinal tumor has been removed, thereby minimizing the secondary undesirable processes previously described herein. Shunting the fluid-filled cyst reduces pressure buildup within the cord and decreases injury to neurons. Bridging the gap formed by the cyst allows a pathway for regrowing neurons to reach the caudal side and form functional synapses.

The term "biodegradable" as used herein means any material that is broken down (usually gradually) by the body of an animal, e.g., a primate mammal, after implantation. The term "bioabsorbable" as used herein means a material or article that is absorbed or resorbed by the body of an animal, e.g., a primate mammal, after implantation such that it eventually becomes essentially non-detectable at the site of implantation. The terminology "biodegradable" or "bioabsorbable" means any material that is biocompatible, as well as biodegradable and/or bioabsorbable. Such materials are capable of being formed into articles that are suitable for implantation into an animal and capable of being biodegraded or bioabsorbed by the animal. Biodegradable or bioabsorbable articles include, but are not limited to biodegradable and bioabsorbable polymers. Examples of suitable polymers are described in Bezwada et al. "Poly(p-Dioxanone) and its Copolymers," in Handbook of Biodegradable Polymers, A. J. Domb, et al., Eds., Hardwood Academic Publishers, The Netherlands, pp. 29-61 (1997).

The articles described herein, including mini-tubes and formable articles, may be incorporated with any number of medically useful substances. For example, the inner or outer surfaces of a mini-tube may be seeded with stem cells; for example, mesenchymal or neuronal stem cells. Such cells may be deposited onto the inner (lumen in the case of the mini-tubes) or outer surface(s). The incorporation of stem cells provides for trophic support or cellular replacement at the site of injury. Furthermore, the biocompatible and biodegradable polymeric articles, including mini-tubes, may additionally, alternatively, or optionally contain pharmaceutically or biologically active substances such as, for example, anti-inflammatory compounds, growth factors, and stem cells, among other medicinal agents.

Also described herein is a kit for surgically treating spinal cord injuries. The kit may include any combination of the components, devices, and polymeric biocompatible materials or articles, in one or more containers, including but not limited to one or more of pre-cut polymeric bandage or mini-tube articles; one or more pieces of artificial dura; trimming tools; alignment tools; drapes; and instructions for using the foregoing in the surgical methods described herein. The components of the kit may be packaged in a sterile manner, using sterile technologies known in the relevant art.

Biocompatible Polymers

Biocompatible polymers (including biodegradable and bioabsorbable polymers) for the fabrication of the herein-described mini-tubes, formable bandage, or neuropatch articles are well-known in the art. For example, the biocompatible polymers may be biodegradable (for example, PLGA). As used herein, "biodegradable" and "erodible" are used interchangeably. Examples of biocompatible polymers that are biodegradable include, but are not limited to, biodegradable hydrophilic polymers such as polysaccharides, proteinaceous polymers, soluble derivatives of polysaccharides, soluble derivatives of proteinaceous polymers, polypeptides, polyesters, polyorthoesters, and the like. The polysaccharides may include poly-1,4-glucans, e.g., starch glycogen, amylose and amylopectin, and the like. Suitable biodegradable hydrophilic polymers include water-soluble derivatives of poly-1, 4-glucan, including hydrolyzed amylopectin, hydroxyalkyl derivatives of hydrolyzed amylopectin such as hydroxyethyl starch ("HES"), hydroxyethyl amylase, dialdehyde starch, and the like. Proteinaceous polymers and their soluble derivatives include gelation biodegradable synthetic polypeptides, elastin, alkylated collagen, alkylated elastin, and the like. Biodegradable synthetic polypeptides include poly-(N-hydroxyalkyl)-L-asparagine, poly-(N-hydroxyalkyl)-L-glutamine, copolymers of N-hydroxyalkyl-L-asparagine and N-hydroxyalkyl-L-glutamine with other amino acids. Suggested amino acids include L-alanine, L-lysine, L-phenylalanine, L-leucine, L-valine, L-tyrosine, and the like.

The aforementioned biodegradable hydrophilic polymers are particularly suited for the methods and compositions hereof by reason of their characteristically low human toxicity and virtually complete biodegradability. Of course, it will be understood that the particular polymer used may be any of a variety of biodegradable hydrophilic polymers may be used.

In yet another embodiment, a biodegradable or bioabsorbable polymer contains a monomer of a glycolide, lactide, dioxanone, caprolactone, trimethylene carbonate, ethylene glycol, or lysine. By the terminology "contains a monomer" is intended a polymer that is produced from the specified monomer(s) or contains the specified monomeric unit(s). The polymer can be a homopolymer, random or block co-polymer or hetero-polymer containing any combination or blend of one or more such monomers.

For example, a biodegradable or bioabsorbable polymer may contains bioabsorbable and biodegradable linear aliphatic polyesters such as polyglycolide ("PGA") and its random copolymer poly(glycolide-co-lactide) ("PGA-co-PLA"). The United States Food & Drug Administration ("FDA") has approved these polymers for use in surgical applications, including medical sutures. An advantage of these synthetic absorbable materials is their degradability by simple hydrolysis of the ester backbone in aqueous environments such as body fluids. The degradation products are ultimately metabolized to carbon dioxide and water or can be renally excreted, unlike cellulose-based materials, which cannot be absorbed by the body.

The molecular weight ("MW") of the polymers used in the articles described herein can vary according to the polymers used and the degradation rate desired to be achieved. In an embodiment, the average MW of the polymers in a fabricated bandage is between about 1,000 and about 50,000. In another embodiment, the average MW of the polymers in a fabricated bandage is between about 2,000 and about 30,000. In yet another embodiment, the average MW is between about 20,000 and about 50,000 for PLGA, and between about 1,000 and about 3,000 for polylysine.

Figure 1:
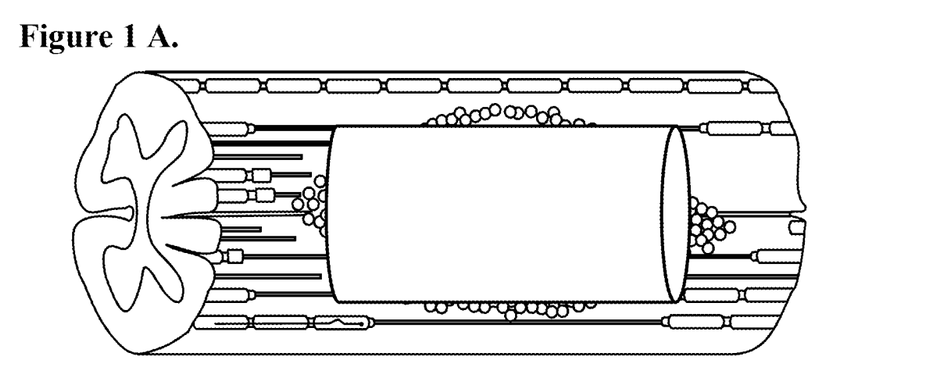
FIGS. 1A and 1B include two schematic representations of exemplary biodegradable protective tubular articles inserted around the locus of a spinal cord injury site, such as a tumor locus after surgical recessing, in accordance with an example embodiment hereof.

An example embodiment includes a biocompatible polymer that is an electrically conductive material. This material allows conduction of endogenous electrical activity from surviving neurons, thereby promoting cell survival. Any such material should be bioresorbable in situ, such that it naturally erodes once its function has been performed. Finally, a three-dimensional scaffold creates a substrate by which cells can be grown in vitro and then implanted in vivo. A hollow cylindrical scaffold (mini-tube) made of polypyrrole ("PPy"), for example, meets all of these design requirements. A schematic exemplary design in situ is shown in FIG. 1.

Electrical signals in the form of action potentials are the means of signaling for billions of cells in the central nervous system. Numerous studies have shown that this electrical activity is not only a means of communication, but also necessary for the normal development of the nervous system and refinement of functional neural circuits. In the case of spinal cord surgery, cell-to-cell communication may be interrupted and the mechanisms of normal neurological development imply that electrical activity should be part of the restoration of functional connections. Such activity is important for the survival of existing cells and the incorporation of any transplanted cells (such as neural stem cells) into working circuits.

Accordingly, in an embodiment, single- and double-layer scaffolds, mini-tubes, and other articles are fabricated from biomaterials that are capable of conducting electricity and naturally biodegrading or eroding inside the body over a preselected period of time. In an exemplary embodiment, single scaffold, double scaffold, or mini-tube articles comprise a biocompatible polymer capable of conducting electricity, such as a polypyrrole polymer. Polyaniline, polyacetyline, poly-p-phenylene, poly-p-phenylene-vinylene, polythiophene, and hemosin are examples of other biocompatible polymers that are capable of conducting electricity and may be used in the articles and methods described herein. Other erodible, electronically conducting polymers are well known. See, e.g., Zelikin et al., "Erodible Conducting Polymers for Potential Biomedical Applications," Angew. Chem. Int. Ed. Engl. 41(1), 141-44 (2002). Any of the foregoing electrical conducting polymers can also be applied or coated onto a malleable or moldable article. The coated article can be also be used as a bandage or neuropatch as described herein.

Tubular Polymeric Biocompatible Articles

"Mini-tubes" and "tubular articles" are provided as cylindrical medical devices or as devices capable of being formed into tubes, as described more fully herein. Exemplary embodiments hereof are directed to biocompatible polymeric articles and materials that can be fabricated into such "mini-tubes" or "tubular articles." These articles and materials can be used to promote post-operative healing of the spinal column and to treat the spinal column after a tumor has been removed therefrom. In an embodiment, one or more mini-tubes are inserted into the spinal column around the location (locus) from which a tumor was removed, such that each hollow tube runs through or around the tumor site preferably parallel to the longitudinal axis of the spinal cord. See, e.g., FIG. 1. The mini-tube can be inserted through a surgical incision made rostral or caudal to the tumor locus. The mini-tube creates a new interface within the spinal cord parenchyma, and it relieves the site of pressure and protects tissue that has been spared from injury. Pressure resulting from the compression force exerted on the cord is alleviated by diffusing or redirecting the force down the surface of the mini-tube and away from the initial compressed site, and absorbing the compression energy into the biocompatible material of the mini-tube. Furthermore, by providing a structure between the injured site and surrounding tissue (the new interface), inflammation may be mitigated in the adjacent area, whereby functionally relevant residual cord tissue can be spared from further trauma.

In another embodiment, biocompatible polymeric electrically conducting articles may be fabricated into hollow mini-tubes or tubular articles having an inner surface, an outer surface, and two opposite open ends. Such articles, including mini-tubes, may be fabricated into any geometrical shape and size. For example, the size and the shape of the article may be varied depending on the age or size of the animal or human patient in which the article is to be used. The size and shape may also be configured to the size of injury remaining after the tumor has been surgically removed. A thin, elongated cylinder is one possible configuration, but other shapes, such as elongated rectangles, spheres, helical structures, and others are possible. For example, such shapes are hollow and open-ended.

Additional alterations in configuration, such as the number, orientation, and shape of the articles may be varied according to sound medical judgment. For instance, the articles may be a rectangular sheet, or any other useful shape that may be rolled up into a cylinder, and may be distributed along or around the locus from which a tumor has been removed. For example, a mini-tube can be smaller than, the same size as, or longer than the surgical lesion to be treated. Furthermore, a mini-tube may be longer than the length of the injured site. In an alternative embodiment, the length of an article (e.g., mini-tube) to be surgically implanted is approximately between 1.2 and about 3 times (or even about 5 times to about 10 times) the length of the injured site or lesion running lengthwise along the spinal cord. In yet another embodiment, a mini-tube extends beyond the caudal and rostral sides of the injured site at a distance of approximately ¼ to ½ the length of the injured site. In yet another embodiment, a mini-tube extends equally beyond the caudal and rostral sides of the injured site.

When a polymeric biocompatible article is in the form of a mini-tube, its diameter (outer surface to outer surface; or "outside diameter") can range from about 0.1 microns to about 10 millimeters or even as large as several millimeters. For example, the overall diameter of the mini-tube (outer surface to outer surface) may be between about 5 microns and about 200 microns or, in some embodiments, several millimeters. In other embodiments, the diameter of the mini-tube (outer surface to outer surface) is between about 20 microns and about 200 microns, between about 50 microns and about 175 microns, between about 100 microns and about 200 microns, or between about 150 microns and about 300 microns. In another embodiment, the diameter of the mini-tube (outer surface to outer surface) is between about 0.5 millimeters and about 20 millimeters. In still other embodiments, the diameter of the mini-tube (outer surface to outer surface) is between about 1 millimeter and about 10 millimeters, between about 1 millimeter and about 5 millimeters, between about 1 millimeter and about 3 millimeters. In other embodiments, the mini-tube may have a diameter of 1 centimeter or larger, depending on its intended application.

Moreover, the diameter of a mini-tube (inner surface to inner surface; also known as the "lumen diameter") can range from microns to millimeters. For example, the diameter of a mini-tube (lumen diameter) may be between about 5 microns and about 200 microns. In other embodiments the diameter of a mini-tube (lumen) may be between about 20 microns and about 200 microns, between about 50 microns and 175 microns, between about 100 microns and about 200 microns, and between about 150 microns and about 300 microns. In still another embodiment, the diameter of a mini-tube (lumen) may be between about 0.5 millimeters and about 15 millimeters. In other embodiments, the diameter of a mini-tube (lumen) may be between about 1 millimeter and about 10 millimeters, between about 1 millimeter and about 5 millimeters, or between about 1 millimeter and about 3 millimeters or larger. In other embodiments, the mini-tube may have a diameter of 1 centimeter or larger, depending on its intended application.

A biodegradable or bioabsorbable polymeric tubular article can be formed by any means. In one embodiment, it is formed by electrodeposition of an electrical conducting polymer onto a template conductive wire, wherein the polymer is released from the wire by applying a reverse potential to the template conductive wire in a saline solution.

Figure 2:
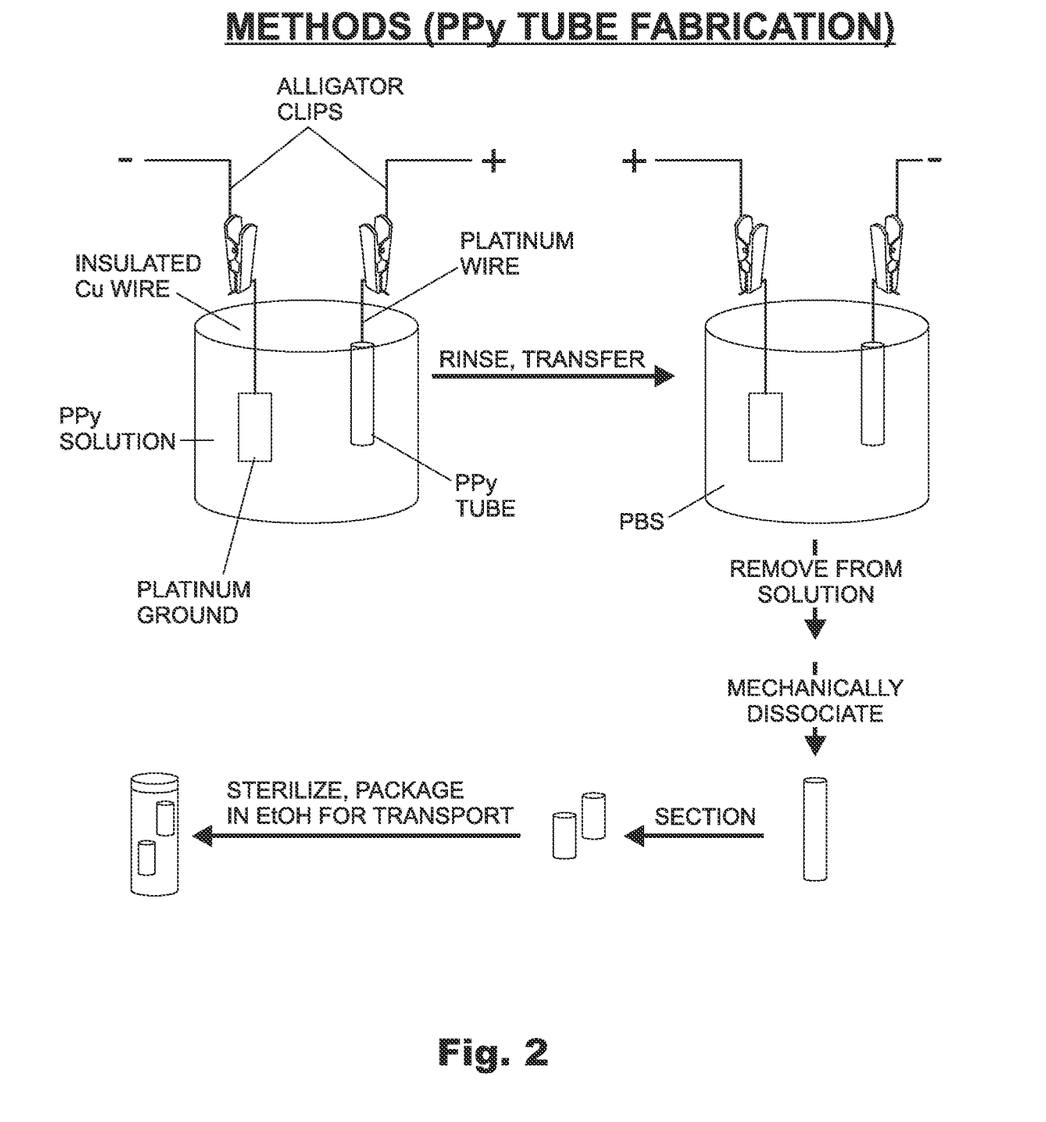
FIG. 2 schematically illustrates an exemplary method of manufacture by electrodeposition of erodible polypyrrole ("PPy") to form protective tubular articles in accordance with an example embodiment hereof.

An example method used to fabricate polymeric mini-tubes described herein is shown in FIG. 2. The pattern of the conductive template for electrodeposition of polypyrrole ("PPy"), for example, controls the shape of the PPy scaffold that is created. By controlling the template, the polymer scaffold can be manufactured in different shapes and sizes, ranging from thin lines to rectangular planar implants, among others. Tube-like PPy scaffolds can be produced by plating the PPy onto a conductive wire. For scaffold removal from the template, a reverse potential is applied to the template in a saline solution. When applied for sufficient time and strength, the scaffold slides off the wire mold with a slight pull. This method relieves the manufacturer of having to use organic solvents to etch the inner wire template, which would yield polymeric articles that are ill-suited for use in vivo. As previously mentioned, polymeric articles, including mini-tubes, may be fabricated into any medically desirable geometrical shape and size.

For example, a cord lesion that is 10 microns in length (running along the length of the spinal cord) and 3 microns deep, may require use of or insertion of a polymeric mini-tube of 15 microns in length (or longer) and having an overall diameter of 2.5 microns. The polymeric mini-tube is surgically inserted through the lesion such that the central section of the lesion is encapsulated by the tube. In this example, the tube will extend approximately 2.5 microns beyond each of the caudal and rostral ends of the target lesioned area.

Moldable Polymeric Biocompatible Articles

A polymeric electrically conducting article for use in the surgical methods described herein may also be provided as a formable, moldable, biocompatible polymeric material or composition. "Moldable" and "formable" are used interchangeably in the present description. Advantageously, a polymeric material may be fabricated as a putty. By "putty" it is meant that the material has a dough-like consistency that is formable or moldable. Such materials are sufficiently and readily moldable and can be formed into flexible three-dimensional structures or shapes complementary to a target site to be treated.

In yet another embodiment, the polymeric biocompatible materials can be fabricated into readily formable or moldable bandages or neuropatches. For example, after spinal tumor removal, a bandage, putty, or neuropatch is formed, whether by hand or by mechanical means, to complement the injured site. The formed article is then implanted into the epicenter of the injury, wherein it fills in the injury site. The implanted article bridges any gap formed by the spinal cord lesion and functions as an artificial pathway, nurturing regrowing neurons, reorganizing neurites and helping to form functional synapses. This new interface allows for interactions between endogenous neural cells (including neural stem cells, if incorporated onto the bandage) and the inhibitory molecule-free polymer implant environment to promote cell survival. Furthermore, by providing a structure between the injured site and surrounding tissue (the new interface), inflammation may be mitigated in the adjacent area where functionally relevant residual cord tissue can be spared.

In an embodiment, polymeric biocompatible bandages may be readily fabricated or formed into any shape and size, including a single polymeric scaffold having an inner surface and an outer surface. For example, the size and the shape of the bandage may be varied in order to deliver more effective relief. A thin, elongated bandage is an exemplary configuration, but other shapes, such as elongated rectangular bandages, spheres, helical structures, and others are possible. Additional alterations in configuration, such as the number, orientation, and shape of the bandages may be varied in order to deliver more effective relief. For instance, the bandages may be rectangular, or any other useful shape, and may be distributed within or around the epicenter (locus) of the spinal cord injury.

In addition, the article may have a textured surface including a plurality of pores or microgrooves on its inner or outer surface. Such pores may have diameters between. For example, about 0.5 microns to about 4 microns and depths of at least about 0.5 microns. Furthermore, microgrooves may have widths of between, for example, about 0.5 microns and about 4 microns and depths of at least about 0.5 microns. The sizes of the article and the sizes and diameters of its pores and microgrooves vary accordingly with the spinal cord lesion to be treated. The pores or microgrooves on the inner or outer surface may be seeded with one or more medicinal agents, for example human neuronal stem cells to provide cellular replacement and trophic support. Alternatively, additionally or optionally, other medicinal agents may be provided such as therapeutic agents, including anti-inflammatories, etc. For example, a moldable article may act as a filler (i.e., fill the lesion) after implantation within the lesioned area of the spinal cord. In another embodiment, the article inner surface is flush with the lesioned spinal cord, i.e., contacts the lesion, when it is implanted.

In another embodiment, a polymeric "fill-in" bandage may be used for the surgical treatment of spinal cord tumors. For example, an erodible, or biodegradable, form of biocompatible polymer may be fabricated for surgical implantation into the site of the spinal cord tumor. The implantation can be accomplished immediately after molding the bandage to conform to the injured site so that the target area is encapsulated by or filled in with the formed polymer. The implantation may result in complete encapsulation of the target area or only a central necrotic area, or it may result in a previously open lesioned area being filled in with the formed polymer. Encapsulation of a central necrotic area minimizes secondary injury by inhibiting cell-cell signaling with inflammatory cytokines. Bridging the gap formed by the lesion allows a pathway for regrowing neurons to reach the caudal side and the formation of functional synapses.

In another embodiment, biocompatible polymeric bandages can be readily fabricated/formed into any shape and size, comprising a single polymeric scaffold having an inner surface and an outer surface, wherein the formed bandages may be fabricated into any geometrical shape and size. This single polymeric scaffold may include pores (for example, on the surface making contact with the lesion) for incorporating medicinal agents such as depositing neural stem cells, drugs, etc.

Optionally, an electrically conductive formable and biocompatible polymeric material may be used to allow conduction of endogenous electrical activity from surviving neurons, thereby promoting cell survival. Any such material should be bioresorbable in situ, such that it naturally erodes once its function has been performed. Finally, a three-dimensional scaffold creates a substrate by which cells can be grown in vitro and then transplanted in vivo. A bandage scaffold made of polypyrrole ("PPy"), for example, meets all of these design requirements.

Polymeric bandages are not limited to electrical conducting polymers, such as PPy. Polymeric bandages may include one or more monomers such as a glycolide, lactide, dioxanone, caprolactone, trimethylene carbonate, ethylene glycol and lysine, for example. Furthermore, it is possible for the polymeric bandages to comprise one or more biodegradable or bioabsorbable linear aliphatic polyesters, copolymer poly (glycolide-co-lactide), or material derived from biological tissue. Material derived from biological tissue can be, but is not limited to, neuronal or mesenchymal stem cells, which can be used as medicinal agents.

As previously mentioned, the mini-tubes, biocompatible and biodegradable polymeric bandages may contain medicinal agents, including pharmaceutically or biologically active substances such as, for example, anti-inflammatory compounds, growth factors, and stem cells. As described above, the polymer bandages may be fabricated into structures wherein the outer surface is an outer scaffold having long, axially oriented pores for axonal guidance or radial pores to allow fluid transport and inhibit in-growth of scar tissue. The inner surface, or inner scaffold, may be porous and seeded with one or more medicinal agents, for example human neuronal stem cells for cellular replacement and trophic support. Therefore, the fabricated and formed bandage may comprise two scaffolds (a double scaffold) and simulate the architecture of a healthy spinal cord through an implant having a polymer scaffold, perhaps seeded with neuronal stem cells. The inner scaffold emulates the gray matter; the outer portion emulates the white matter. The bandage can be readily designed to be tailored to fit into a variety of cavities.

In another embodiment, a medical article suitable for implanting within an animal or human spinal cord includes a moldable biocompatible material comprising a roughly equal (e.g., 50:50) blend of poly(lactic-co-glycolic acid) and a block copolymer of poly(lactic-co-glycolic acid)-polylysine. The poly(lactic-co-glycolic acid) is 75% poly(lactic-co-glycolic acid), wherein the average molecular weight (Mn) is about 40,000. The block copolymer of poly(lactic-co-glycolic acid)-polylysine is 25% poly(lactic-co-glycolic acid)-polylysine copolymer, wherein the average molecular weight of the poly(lactic-co-glycolic acid) block (Mn) is about 30,000 and the average molecular weight (Mn) of the polylysine block is about 2,000. In an alternative embodiment, the article includes a single block of poly(lactic-co-glycolic acid).

Any of the foregoing articles may a degradation rate in vivo of about between about 30 and about 60 days (e.g., 4 to 6 weeks); however, the rate can be altered to provide a desired level of efficacy of treatment within sound medical judgment. The article may further comprise medicinal agents such as stem cells in association with any of the polymeric material.

For example, the stem cells may be seeded onto the polymer or, more specifically, seeded within pores on the surface of the polymer. Any stem cell type may be used, although for the treatment of spinal cord tumors, neuronal stem cells and mesenchymal stem cells are of especial utility.

In yet another example embodiment, a method is disclosed for treating an spinal cord wound resulting from tumor removal, the method including providing a double scaffold of polypyrrole to conform to a lesioned area of the spinal cord injury, and thereafter filling in the lesioned area with the biocompatible polypyrrole material. The inner surface, or inner scaffold, may be porous and seeded with one or more medicinal agents, for example human neuronal stem cells for cellular replacement or trophic support.

Such a fabricated and formed bandage therefore includes two scaffolds and simulates the architecture of a healthy spinal cord through an implant made of a polymer scaffold, optionally seeded with neuronal stem cells. The inner scaffold emulates gray matter, while the outer scaffold (the second scaffold) emulates white matter by having, for example, long, axially oriented pores for axonal guidance and radial porosity to allow fluid transport and inhibiting in-growth of scar tissue. Such a bandage can be readily designed to be tailored to fit into a variety of cavities, and to provide a pre-selected degradation, erosion, or medicinal agent release profile.

In an example embodiment, polypyrrole has a degradation rate of about between about 30 and 60 days (e.g., 4 to 6 weeks); however, the rate can be altered to provide a desired level of efficacy of treatment. The material may further comprise stem cells in association with any of the polymeric material. For example, the stem cells may be seeded onto the polymer or, more specifically, seeded within pores on the surface of the polymer. Any stem cell type may be used, although for the treatment of spinal cord tumors, the stem cells advantageously include neuronal stem cells or mesenchymal stem cells.

EXAMPLE EMBODIMENTS

So that the scope and usefulness of the methods and devices disclosed herein may be better understood, the following illustrative, non-limiting embodiments are provided for the reader's benefit.

For example, a method for the treatment of hyperproliferative diseases affecting the spinal cord includes medical treatment of an animal or human subject in need thereof, including steps of removing at least a portion of a tumor from a locus of an animal or human spinal column, and thereafter implanting a polymeric biocompatible article into the spinal column of the animal or human, wherein the polymeric biocompatible article is biodegradable or bioabsorbable in vivo.

For example, the polymeric biocompatible article may be electrically conducting. In an embodiment, the polymeric biocompatible article is comprised of a synthetic bioabsorbable polymer.

In the methods herein, implanting step may include implanting the polymeric biocompatible article into the animal or human spinal column proximate adjacent to the locus such that the polymeric biocompatible article at least partially surrounds the locus of the tumor after surgical recessing thereof.

In an example embodiment, the polymeric biocompatible article is substantially tubular. In another embodiment, the polymeric biocompatible article is a hollow tube. For example, the polymeric biocompatible article may form a tube having a diameter of between about 0.1 microns and about 10 millimeters. The diameter may be between about 50 microns and about 175 microns. Similarly, the polymeric biocompatible article may longer than the spinal tumor tissue. For example, the polymeric biocompatible article may be at least about 1.5 times longer than the locus.

Typically, the polymeric biocompatible article completely yet gradually resorbs after implantation. For example, the polymeric biocompatible article may have a degradation rate of about between about 30 and about 60 days (or between about 4 weeks and about 6 weeks) in vivo.

The polymeric biocompatible article may be comprised of one or more polymers selected from the group consisting of polypyrrole polymer, polyaniline, polyacetyline, poly-p-phenylene, poly-p-phenylene-vinylene, polythiophene, hemosin, and combinations thereof. For example, the one or more polymers may include polypyrrole. In another embodiment, the one or more polymers may include one or more repeating monomers selected from the group consisting of a glycolide, lactide, dioxanone, caprolactone, trimethylene carbonate, ethylene glycol, lysine, and combinations thereof. By way of further example, the one or more polymers may include a biodegradable or bioabsorbable linear aliphatic polyester, such as polyglycolide or poly(glycolide-co-lactide).

In still yet another embodiment, the polymeric biocompatible article may consist essentially of a single scaffold of a moldable biocompatible material comprising poly(lactic-co-glycolic acid). Additionally, the poly(lactic-co-glycolic acid) may be 75% poly(lactic-co-glycolic acid), the average molecular weight (Mn) being between about 20,000 and about 50,000. In another embodiment, the polymeric biocompatible article consists essentially of about a 50:50 blend of poly(lactic-co-glycolic acid) and a block copolymer of poly(lactic-co-glycolic acid)-polylysine. In still a further embodiment, the block copolymer of poly(lactic-co-glycolic acid)-polylysine is about 25% poly(lactic-co-glycolic acid)-polylysine copolymer and the poly(lactic-co-glycolic acid) block has an average molecular weight (Mn) of between about 20,000 and about 50,000 and the polylysine block has an average molecular weight (Mn) of between about 1,000 and about 3,000.

The polymeric biocompatible article may also be a moldable biocompatible polymeric material comprising an electrically conducting polymer. For example, the electricity conducting polymer may be selected from the group consisting of a polypyrrole polymer, a polyaniline, a polyacetyline, a poly-p-phenylene, a poly-p-phenylene-vinylene, a polythiophene, a hemosin, and combinations thereof.

The polymeric biocompatible article may also include one or more medicinal agents compatible with spinal column neural regeneration or healing. The one or more medicinal agents that stimulate spinal column regeneration or healing assist the animal or human to recover motorsensory function after spinal tumor surgery. In an example configuration, the polymeric biocompatible article is a tube and the one or more medicinal agents are contained on an inner surface of the tube.

The one or more medicinal agents that stimulate spinal column regeneration or healing comprise one or more therapeutic medicines. For example, the one or more therapeutic medicines may include anti-inflammatory compounds, anti-cancer agents, anti-oxidant free radical scavengers, wound healing promoters, pain-controlling agents, neuroplasticity enhancers, and anti-degeneration compounds. Furthermore, the one or more medicinal agents that stimulate spinal column neural regeneration or healing are on a surface of the polymeric electrically conducting article. The one or more medicinal agents that stimulate spinal column regeneration or healing may include one or more donor neuronal cells, such as one or more human neuronal stem cells. For example, the one or more medicinal agents that stimulate spinal column regeneration or healing may include one or more mesenchymal stem cells.

In another embodiment, a method of medical treatment of an animal or human subject in need thereof includes steps of removing at least a portion of a tumor from a locus within an animal or human spinal column, molding a polymeric biocompatible material consisting essentially of a single scaffold article comprising poly(lactic-co-glycolic acid), and thereafter implanting the polymeric biocompatible material into the spinal column of the animal or human proximate to the locus such that the polymeric biocompatible material at least partially surrounds the locus of the tumor after surgical recessing thereof. The stem cells may be in association with the polymeric biocompatible material.

Also provided herein is a kit for use in a medical treatment of an animal or human subject in need thereof including in one or more containers one or more polymeric biocompatible articles and instructions for use thereof in a surgical method for removing at least a portion of a tumor from an animal or human spinal column. The kit may also include one or more pieces of artificial dura or one or more trimming tools.

In yet another embodiment, a method of medical treatment of an animal or human subject in need thereof includes the steps of surgically exposing a surgical site to provide surgical access to a spinal column containing a tumor, resecting at least a portion of the tumor thereby providing an implantation site for a polymeric biocompatible article, implanting the polymeric biocompatible article into the implantation site, and thereafter surgically closing the surgical site.

In a still further embodiment, a method of medical treatment of an animal or human subject in need thereof includes the step of instructing a medical caregiver to implant a polymeric biocompatible article into a spinal column of an animal or human subject after surgical recessing of at least a portion of a tumor from the spinal column.

EXAMPLES

Example 1

Polypyrrole Mini-Tube Fabrication (I)

Polypyrrole tube scaffolds are created by electrodeposition of erodible PPy at 100 µA for 30 minutes onto 250 µm diameter platinum wire. See, e.g., FIG. 2. This step is followed by reverse plating at 3 V for 5 minutes, allowing for the removal of the scaffold. The current, timing, voltage, and other parameters of the example are not intended to be limiting.

Example 2

Fabrication of PPy Mini-Tubes (II)

Tube-like PPy scaffolds were produced by plating the PPy onto a conductive wire mold. This technique can be scaled to produce scaffolds of any length, inner diameter, and outer diameter. Furthermore, surface roughness can be controlled with electroplating temperature (see, FIG. 2). Scaffold extraction from the template is achieved by application of a negative potential in a saline solution. The negative potential causes electrochemical reduction and slightly increases the size of the scaffold. It can then be mechanically dissociated from the platinum wire mold with minimal applied force, resulting in no damage to the material. This technique is an improvement over prior methods of etching the inner wire with harsh organics. For in vivo use, PPy tube scaffolds were created by electrodeposition of erodible PPy at 100 µA for 40 min onto 250 µm diameter platinum wire, followed by reverse plating at 3V for 20 seconds, which allows for removal of the scaffold. The resulting tubes of 10-15 mm length were sectioned into 3 mm long pieces for implantation.

Example 3

Single Scaffold Fabrication

A single scaffold was fabricated from a blend of 50:50 poly(lactic-co-glycolic acid) (PLGA) (75%, number average molecular weight, Mn, ~40,000) and a block copolymer of poly(lactic-co-glycolic acid)-polylysine (25%, PLGA block Mn ~30,000, polylysine block Mn ~2000). The PLGA was chosen to achieve a pre-selected degradation rate of about 30-60 days, and the functionalized polymer was incorporated to provide sites for possible surface modification. The single scaffold was made using a salt-leaching process: A 5% (wt/vol) solution of the polymer blend in chloroform was cast over salt with a diameter range of 250-500 µm, and solvent was allowed to evaporate. The salt was then leached in water, producing a single porous polymer layer that can be seeded with stem cells or other medicinal agents.

Example 4

Double Scaffold Fabrication

Both the inner and outer scaffolds were fabricated from a blend of 50:50 poly(lactic-co-glycolic acid) (PLGA) (75%, number average molecular weight, Mn, ~40,000) and a block copolymer of poly(lactic-co-glycolic acid)-polylysine (25%, PLGA block Mn ~30,000, polylysine block Mn ~2000). The PLGA was chosen to achieve a degradation rate of about 30-60 days, and the functionalized polymer was incorporated to provide sites for possible surface modification. The inner scaffold was made using a salt-leaching process: a 5% (wt/vol) solution of the polymer blend in chloroform was cast over salt with a diameter range of 250-500 µm, and the solvent was allowed to evaporate. The salt was then leached in water. The oriented outer scaffold was fabricated using a solid-liquid phase separation technique in the following manner: A 5% (wt/vol) solution of the polymers was filtered and injected into silicone tubes which were lowered at a rate of $2.6 \times 10^4$ m/s into an ethanol/dry ice bath. Once frozen, dioxane was sublimated using an industry standard temperature-controlled freeze drier. The scaffolds were then removed, trimmed, assembled, and stored in a vacuum desiccator until use. The resulting product has an inner scaffold that emulates gray matter via a porous polymer layer that can be seeded with stem cells, and the outer scaffold emulates the white matter with long, axially oriented pores for axonal guidance and radial porosity to allow fluid transport while inhibiting in-growth of scar tissue.

Example 5

Seeding of Murine Neuronal Stem Cells onto Polymer Articles

Murine NSCs (neuronal stem cells) were maintained in serum-containing medium. Scaffolds were soaked in 70% ethanol for 24 hrs, rinsed three times in PBS, and seeded on an orbital shaker with 5×10$^5$ cells/mL at 37° C. in a humidified 5% $CO_2$/air incubator. The medium was changed the next day, and the implants were incubated for four more days before implantation.

Example 6

Seeding of Human Neuronal Stem Cells onto Polymer Articles

Human HFB2050 and HFT0305, cells derived from HFB2050 ("hNSCs"), Redmond et al., 2007, were initially isolated from primary dissociated serum-containing monolayer cultures of the telencephalic ventricular zone of a cadaver as previously described. In an example embodiment, transplantation of hNSCs used the following methods for the generation, maintenance, and grafting of cells. First a primary dissociated, stable serum-containing monolayer culture of fetal ventricular zone was established. A promising culture was then subjected to a six- to eight-week sequential growth factor selection process based on growth parameters rather than on markers. Cells that formed clusters that were greater than ten cell diameters and could not be readily disaggregated were excluded. Both attached and non-attached cells were included. Cells grown in serum were switched to serum-free conditions containing EGF+bFGF. They were passaged once per week for two weeks. Cells that successfully passaged were then grown in basal media and bFGF alone. They were similarly passaged once per week for two weeks. Cells that successfully passaged in bFGF were then switched to EGF alone. They were similarly passaged once per week for two weeks. Cells that successfully passaged in EGF were then switched back to bFGF and a similar two-week selection process was continued. Cells that successfully passaged in bFGF were then switched to bFGF+LIF.

Cultures that had successfully passaged over the previous six to eight weeks and continued to maintain stem-like growth after this selection process were then subjected to in vitro and in vivo functional screens. In vitro, the cells must be able to express undifferentiated markers (nestin, vimentin, sox2, and musashi) yet, in response to induction, express markers consistent with dopamine precursors. The in vivo functional screen entailed continuing to use only those cells that had the ability to engraft, migrate, and differentiate in vivo after implantation into the ventricles and cerebella of newborn (P0) mice and yielded olfactory bulb neurons or cerebellar granule neurons, respectively.

After three to four weeks, the mice were euthanized to determine which hNSCs yielded neurons in the olfactory bulb, glia in the cortex, and granule neurons in the cerebellum. Based on this screening protocol, cell lines were ultimately selected for further use. These lines were expanded and then aliquoted, frozen, and stored as dozens of vials of early passaged hNSCs to be used for future experiments. Resulting human neuronal stem cells may be seeded onto polymeric articles in accordance with the foregoing example.

While this description is made with reference to exemplary embodiments, it will be understood by those skilled in the art that various changes may be made and equivalents may be substituted for elements thereof without departing from the scope. In addition, many modifications may be made to adapt a particular situation or material to the teachings hereof without departing from the essential scope. Also, in the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Finally, it should be noted that the sub-headings provided herein are for the reader's convenience, and they should not be construed as limiting.

The invention claimed is:

1. A method of medical treatment of an animal or human subject experiencing hyperproliferative disease of the spinal cord and inhibiting secondary injury to the spinal cord comprising steps of
   (a) removing at least a portion of a tumor from a locus of an animal spinal cord or human spinal cord; and
   (b) implanting an article into the spinal cord of the animal or human,
   wherein the article is biodegradable or bioabsorbable in vivo,
   wherein the article comprises a single layer polymer scaffold comprising (1) poly(lactic-co-glycolic acid) and (2) a block copolymer of poly(lactic-co-glycolic acid)-polylysine; and
   wherein the implanting step includes implanting the article into the animal spinal cord or human spinal cord proximate to the locus such that the article at least partially surrounds the locus of the tumor after surgical recessing thereof.

2. The method according to claim 1, wherein the article is longer than the spinal tumor tissue.

3. The method according to claim 1, wherein the article is at least about 1.5 times longer than the locus.

4. The method according to claim 1, wherein the article completely yet gradually resorbs after implantation.

5. The method according to claim 4, wherein the article has a degradation rate of between about 30 and about 60 days in vivo.

6. The method according to claim 1, wherein the article comprises one or more medicinal agents that stimulate spinal column neural regeneration or healing.

7. The method according to claim 6, wherein the one or more medicinal agents that stimulate spinal column regeneration or healing assist the animal or human to recover motorsensory function after spinal tumor surgery.

8. The method according to claim 7, wherein the one or more medicinal agents that stimulate spinal column regeneration or healing comprise one or more therapeutic medicines.

9. The method according to claim 8, wherein the one or more therapeutic medicines are selected from the group consisting of anti-inflammatory compounds, anti-cancer agents, anti-oxidant free radical scavengers, wound healing promoters, pain-controlling agents, neuroplasticity enhancers, and anti-degeneration compounds.

10. The method of claim 1, wherein the (1) poly(lactic-co-glycolic acid) has an average molecular weight of between Mn 20,000 and 50,000.

11. The method of claim 1, wherein the scaffold comprises a (1) 50:50 blend of poly(lactic-co-glycolic acid) and a (2) block copolymer of poly(lactic-co-glycolic acid)-polylysine.

12. The method of claim 11, wherein the (2) block copolymer of poly(lactic-co-glycolic acid)-polylysine comprises a poly(lactic-co-glycolic acid) block having an average molecular weight of between Mn 20,000 and 50,000; and a polylysine block having an average molecular weight of between Mn 1,000 and 3,000.

13. The method of claim 1, wherein the scaffold is a cylinder.

14. The method of claim 13, wherein the cylinder is hollow.

15. The method of claim 1, wherein the scaffold is moldable.

16. The method of claim 1, wherein the scaffold has an overall diameter of between 0.1 microns and 10 millimeters.

17. The method of claim 16, wherein scaffold has an overall diameter of between 1 millimeter and 6 millimeters.

18. The method of claim 1, further comprising one or more medicinal agents deposited onto the scaffold.

19. The method of claim 18, wherein the one or more medicinal agents are selected from the group consisting of anti-inflammatory compounds, anti-cancer agents, anti-oxidant free radical scavengers, wound healing promoters, pain-controlling agents, neuroplasticity enhancers, anti-degeneration compounds, growth factors and stem cells.

20. The method of claim 19, wherein the stem cells are selected from the group consisting of neuronal stem cells and mesenchymal stem cells.

21. The method of claim 1, wherein the scaffold is a single porous polymer layer.

22. The method of claim 1, wherein the scaffold consists essentially of (1) poly(lactic-co-glycolic acid) and (2) a block copolymer of poly(lactic-co-glycolic acid)-polylysine.

23. A method of medical treatment of an animal or human subject experiencing hyperproliferative disease of the spinal cord and inhibiting secondary injury to the spinal cord comprising steps of
(a) surgically exposing a surgical site to provide surgical access to a spinal cord containing a tumor;
(b) resecting at least a portion of the tumor thereby providing an implantation site for an article;
(c) implanting the article into the implantation site; and
(d) surgically closing the surgical site,
wherein the article comprises a single layer polymer scaffold comprising (1) poly(lactic-co-glycolic acid) and (2) a block copolymer of poly(lactic-co-glycolic acid)-polylysine, and
wherein the implanting step includes implanting the article into the animal or human spinal cord proximate to the locus such that the article at least partially surrounds the locus of the tumor after surgical recessing thereof.

* * * * *